United States Patent
Corr et al.

(10) Patent No.: US 11,559,507 B2
(45) Date of Patent: *Jan. 24, 2023

(54) PHARMACEUTICAL COMPOSITION

(71) Applicant: MEXICHEM FLUOR S.A. DE C.V., San Luis Potosi (MX)

(72) Inventors: Stuart Corr, Cheshire (GB); Timothy James Noakes, Flintshire (GB)

(73) Assignee: Mexichem Fluor S.A. de C.V., San Luis Potosi (MX)

( * ) Notice: Subject to any disclaimer, the term of this patent is extended or adjusted under 35 U.S.C. 154(b) by 0 days.

This patent is subject to a terminal disclaimer.

(21) Appl. No.: 16/575,168

(22) Filed: Sep. 18, 2019

(65) Prior Publication Data

US 2020/0009089 A1 Jan. 9, 2020

Related U.S. Application Data

(63) Continuation of application No. 15/781,045, filed as application No. PCT/GB2016/053812 on Dec. 2, 2016.

(30) Foreign Application Priority Data

Dec. 4, 2015 (GB) .................................. 1521456
Sep. 19, 2016 (GB) .................................. 1615916

(51) Int. Cl.
| | |
|---|---|
| A61K 31/167 | (2006.01) |
| A61K 9/00 | (2006.01) |
| A61K 31/58 | (2006.01) |
| A61K 31/573 | (2006.01) |
| A61K 31/56 | (2006.01) |

(52) U.S. Cl.
CPC ............ *A61K 31/167* (2013.01); *A61K 9/008* (2013.01); *A61K 9/0073* (2013.01); *A61K 9/0078* (2013.01); *A61K 31/56* (2013.01); *A61K 31/573* (2013.01); *A61K 31/58* (2013.01)

(58) Field of Classification Search
CPC .. A61K 2300/00; A61K 31/167; A61K 31/56; A61K 31/573; A61K 31/58; A61K 9/0073; A61K 9/0078; A61K 9/008
See application file for complete search history.

(56) References Cited

U.S. PATENT DOCUMENTS

| | | | |
|---|---|---|---|
| 5,439,670 A * | 8/1995 | Purewal ................. | A61K 9/008 424/45 |
| 5,776,432 A | 7/1998 | Schultz et al. | |
| 6,103,266 A * | 8/2000 | Tapolsky ............ | A61K 9/7015 424/484 |
| 6,123,924 A | 9/2000 | Mistry et al. | |
| 6,413,497 B1 | 7/2002 | Weil et al. | |
| 6,432,415 B1 | 8/2002 | Osborne et al. | |
| 6,461,591 B1 | 10/2002 | Keller et al. | |
| 6,475,467 B1 | 11/2002 | Keller et al. | |
| 7,105,152 B1 | 9/2006 | Schultz et al. | |
| 7,759,328 B2 | 7/2010 | Govind et al. | |
| 7,897,646 B2 | 3/2011 | Bauer et al. | |
| 8,143,239 B2 | 3/2012 | Govind et al. | |
| 8,461,211 B2 | 6/2013 | Morikawa et al. | |
| 8,575,137 B2 | 11/2013 | Govind et al. | |
| 8,597,616 B2 * | 12/2013 | Kraft ..................... | A61K 31/137 424/46 |
| 9,517,216 B2 * | 12/2016 | Corr ..................... | A61M 15/009 |
| 10,039,828 B2 | 8/2018 | Corr et al. | |
| 10,258,568 B2 * | 4/2019 | Corr ....................... | A61K 47/06 |
| 10,258,569 B2 * | 4/2019 | Corr ....................... | A61K 9/008 |
| 2002/0025299 A1 | 2/2002 | Lewis et al. | |
| 2006/0009437 A1 | 1/2006 | Hassan et al. | |
| 2009/0092559 A1 | 4/2009 | Hoelz et al. | |
| 2010/0143269 A1 | 6/2010 | Sequeira et al. | |
| 2011/0081301 A1 | 4/2011 | Brambilla | |
| 2011/0150783 A1 | 6/2011 | Bonelli et al. | |
| 2012/0111324 A1 * | 5/2012 | Kraft ..................... | A61K 9/0075 128/203.15 |
| 2014/0230812 A1 * | 8/2014 | Corr ..................... | B65B 31/003 128/200.23 |
| 2014/0248357 A1 | 9/2014 | Finch et al. | |
| 2014/0286877 A1 | 9/2014 | Corr et al. | |
| 2015/0182450 A1 | 7/2015 | Bonelli et al. | |

(Continued)

FOREIGN PATENT DOCUMENTS

| | | |
|---|---|---|
| CN | 1296814 A | 5/2001 |
| CN | 102362860 | 2/2012 |

(Continued)

OTHER PUBLICATIONS

Purohit, D., A. Trehan, and V. Arora. "Development of room temperature stable formulation of formoterol fumarate/beclomethasone HFA pMDI." Indian Journal of Pharmaceutical Sciences 71.6 (2009): 713.*

International Search Report for International Application No. PCT/GB2012/051059, 5 pages (dated Aug. 23, 2012).

International Search Report and the Written Opinion of the International Searching Authority for International Application No. PCT/GB2012/051059, 11 pages (dated Sep. 5, 2012).

(Continued)

*Primary Examiner* — Yong S. Chong

(74) *Attorney, Agent, or Firm* — Crowell & Moring LLP

(57) ABSTRACT

A pharmaceutical composition is described. The composition comprises: (i) at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol; (ii) at least one corticosteroid; (iii) a surfactant component comprising at least one surfactant compound; and (iv) a propellant component comprising 1,1-difluoroethane (R-152a).

20 Claims, 4 Drawing Sheets

(56) References Cited

U.S. PATENT DOCUMENTS

| | | | |
|---|---|---|---|
| 2015/0250713 A1 | 9/2015 | Malhotra et al. | |
| 2017/0007701 A1* | 1/2017 | Corr | A61K 9/124 |
| 2017/0027867 A1* | 2/2017 | Corr | A61K 47/10 |
| 2019/0142750 A1 | 5/2019 | Corr et al. | |
| 2019/0247339 A1 | 8/2019 | Corr et al. | |
| 2019/0274973 A1 | 9/2019 | Corr et al. | |

FOREIGN PATENT DOCUMENTS

| | | |
|---|---|---|
| EP | 0 372 777 A2 | 11/1989 |
| EP | 0 653 204 A2 | 11/1989 |
| EP | 0 995 434 A2 | 11/1989 |
| EP | 2 072 051 A1 | 6/2003 |
| EP | 1 870 090 A2 | 12/2007 |
| GB | 2 392 915 A | 3/2004 |
| WO | WO 91/11173 | 8/1991 |
| WO | WO 93/11773 A1 | 6/1993 |
| WO | WO 96/19198 | 6/1996 |
| WO | WO 96/32151 | 10/1996 |
| WO | WO 99/16422 | 4/1999 |
| WO | WO 99/65460 | 12/1999 |
| WO | WO 01/43722 A2 | 6/2001 |
| WO | 01/89480 A1 | 11/2001 |
| WO | WO 03/020253 A2 | 3/2003 |
| WO | 03/063842 A1 | 8/2003 |
| WO | WO 03/086350 A1 | 10/2003 |
| WO | WO2004/015822 | 2/2004 |
| WO | WO 2005/034911 A1 | 4/2005 |
| WO | WO 2005/034927 A2 | 4/2005 |
| WO | WO 2006/004646 A1 | 1/2006 |
| WO | WO 2007/020204 A2 | 2/2007 |
| WO | WO 2008/097233 A1 | 8/2008 |
| WO | WO 2011/023734 A1 | 3/2011 |
| WO | 2012/007729 * | 1/2012 |
| WO | WO 2012/007729 | 1/2012 |
| WO | WO 2012/110770 A2 | 8/2012 |
| WO | WO 2012/156711 | 11/2012 |
| WO | WO 2014/016548 A2 | 1/2014 |
| WO | 2014/064410 A2 | 5/2014 |
| WO | 2014/170689 A1 | 10/2014 |
| WO | WO 2017/093758 A1 | 6/2017 |
| WO | 2007/121913 A2 | 11/2017 |

OTHER PUBLICATIONS

International Preliminary Report on Patentability for International Application No. PCT/GB2012/051059, 4 pages (dated Mar. 1, 2013).

International Search Report and Written Opinion for International Application No. PCT/GB2016/053804, 12 pages (dated Mar. 28, 2017).

International Preliminary Report on Patentability for International Application No. PCT/GB2016/053804, 18 pages (dated Feb. 27, 2018).

Noakes, Tim, "Medical aerosol propellants," Elsevier, Journal of Fluorine Chemistry, 118 (2002) pp. 35-45, Cheshire, UK.

Official Action for BR112018011266-6, dated Jul. 31, 2020, 4 pp.

Brochure, Solkane® 227 pharma and Solkane® 134 pharma, HFA Propellants for Medical Use, Solvay Fluor, Solvay Fluor und Derivate GmbH, www.solvay-fluor.com, 44 pp.

DOE/CE/23810-112, Richard C. Cavestri, Ph.D. and William R. Schafer, Imagination Resources, Inc., Final Report, ASHRAE RP-923, Water Solubility and Clathrate Hydrates in HFC Refrigerants and Refrigerant Blends, 71 pp., Jul. 2000.

Christopher W. Meyer and Graham Morrison, J. Phys. Chem. 1991, 95, 3860-3866, Dipole Moments of Seven Partially Halogenated Ethane Refrigerants, Published 1991 by the American Chemical Society,7 pp.downloaded Mar. 10, 2021 at 15:23:30 (UTC).

Daikin, Positively Innovative, SOLKANE™ 227 pharma and 134a pharma, Smart inhalation—Happy people, Daikin Refrigerants Europe, SOLKANE™ 227 pharma and SOLKANE™ 134a pharma, 42 pp.

Notice of Opposition for EP3383366, dated Jan. 18, 2021, 24 pp.

Orange Book: Approved Drug Products with Therapeutic Equivalence, https://www.accessdata.fda.gov/scripts/cder/ob/patent_info.cfm?Product_No=021929&Appl_type=N, 3 pp.

Medication Guide, Symbicort 80/4.5, Reference ID:2906451, 15 pp.

Advances in Metered Dose Inhaler Technology: Formulation Development, Myrdal et al., AAPS PharmSciTech, vol. 15, No. 2, Apr. 2014 (© 2014), 22 pp.

Encyclopedia of Pharmaceutical Technology, Third Edition, vol. 1, edited by James Swarbrick, PharmaceuTech, Inc., Pinehurst, North Carolina, USA, Informa healthcare, 2007, "Metered Dose Inhalers", Munro et al., 18 pp.

Notice of Opposition for EP Application No. 17777636.6, Beck Greener LLP, dated Aug. 4, 2021, 25 pgs.

Communication of Notice of Opposition for EP Application No. 17777636.6, Beck Greener LLP, dated Aug. 10, 2021 1pg.

Acknowledgement of receipt of Notice of Opposition for EP Application No. 17777636.6, Beck Greener LLP, received Aug. 4, 2021 2pgs.

Cox, Shayne "Pharmaceutical Manufacturing Handbook—Production and Processes" John Wiley & Sons, Hoboken USA 2008 13 pgs.

Ernstgard, Lena, et al. "Uptake and disposition of 1, 1-difluoroethan (HFC-152a) in humans", Toxicology Letters, 209 (2012) 21-29.

Fostair® 100/6 micrograms per actuation pressurized inhalation solution—Summary of product characteristics (updated 2020) available from: https://www.medicines.org.uk/emc/product/6318 12 pgs.

Fostair® 100/6 micrograms per actuation pressurized inhalation solution—Summary of product characteristics, history of changes and changes made (between 2008 and 2020) available form https://www.medicines.org.uk/emc/product/6318 "view changes" 12 pgs.

Purohit D. et al., "Development of Room Temperature Stable Formulation of Formoterol Fumarate/Beclomethasone HFA pMDI" Ind. J. Pharm Sci, (2009) 713-715.

Williams R.O. et al., "Advanced Drug Formulation Design to Optimize Therapeutic Outcomes" Informa Healthcare, CRC Press, Taylor & Francis Group, Boca Raton USA 2008 38 pgs.

* cited by examiner

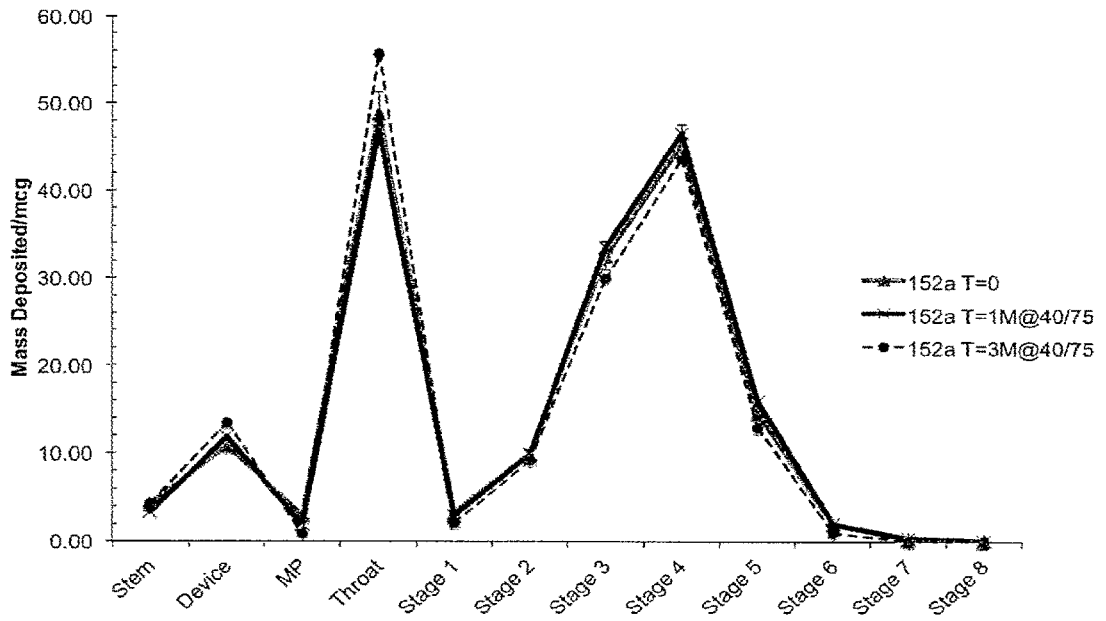
A
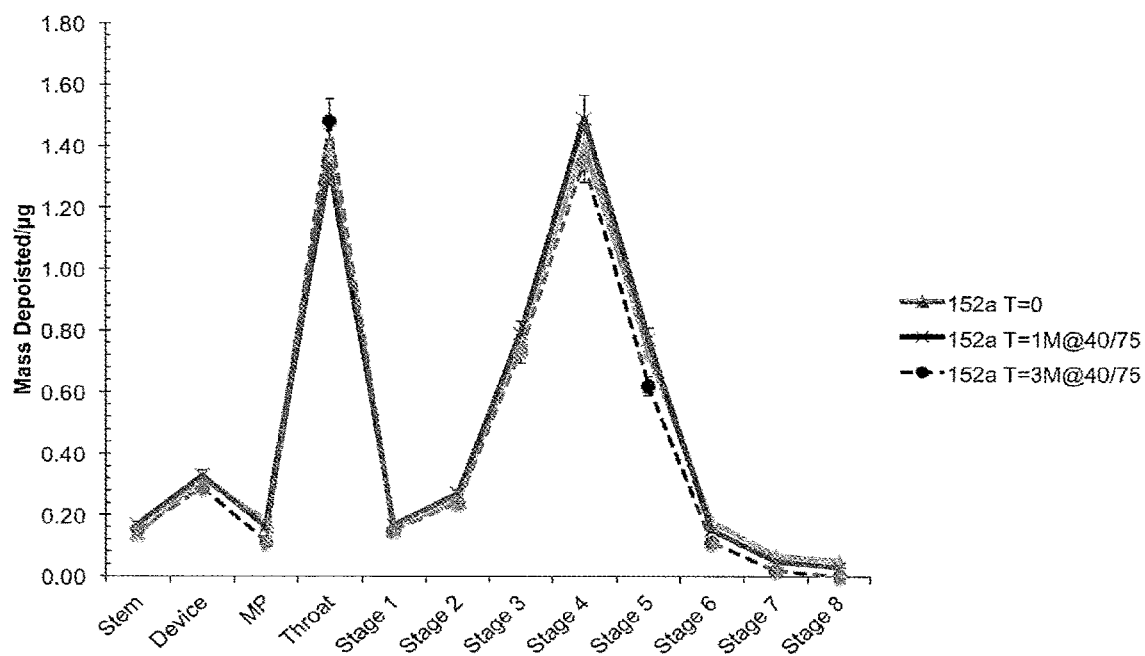
B
Figure 1. APSD profile of budesonide (A) and formoterol (B) actuated from a combination budesonide/formoterol formulation in HFA 152a actuated into a NGI at 30 L.min$^{-1}$.

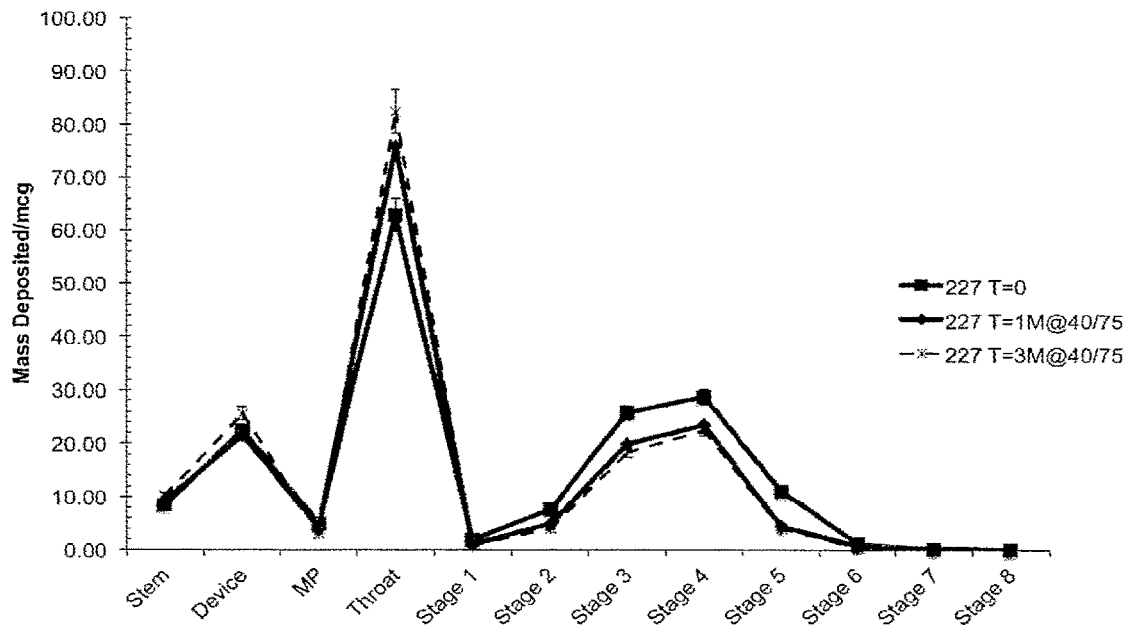
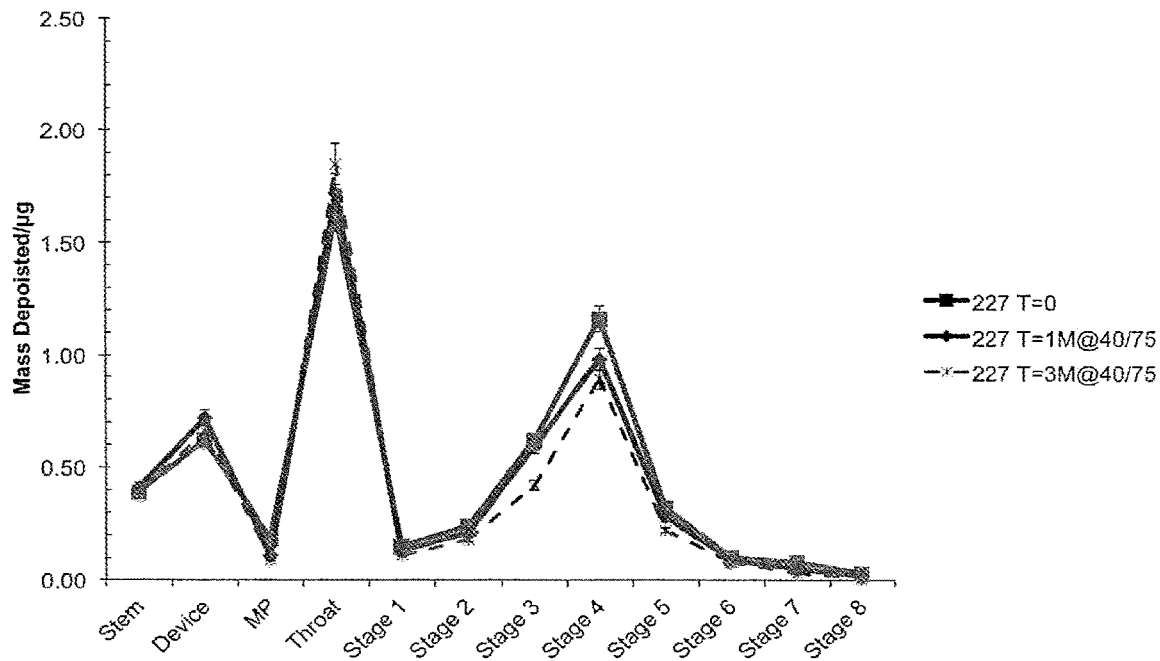
Figure 2. APSD profile of budesonide (A) and formoterol (B) actuated from a combination budesonide/formoterol formulation in HFA 227ea actuated into a NGI at 30 L.min$^{-1}$.

A

B

Figure 3. APSD profile of budesonide (A) and formoterol (B) actuated from a combination budesonide/formoterol formulation in HFA 152a actuated into a NGI at 30 L.min$^{-1}$.

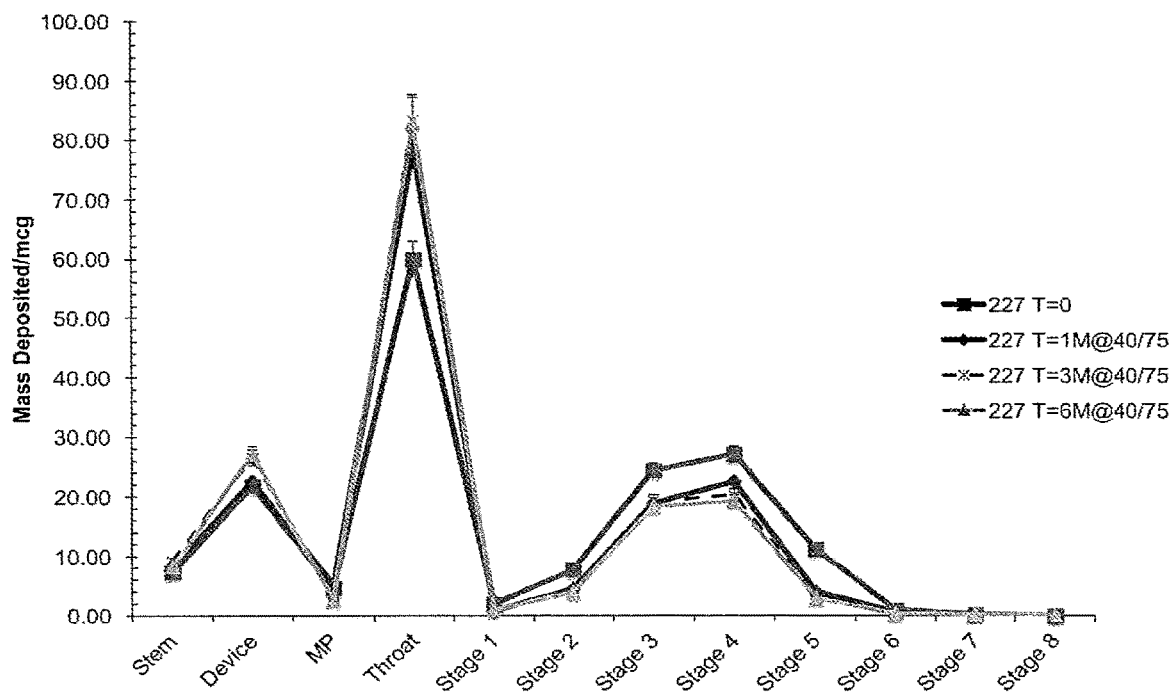
A
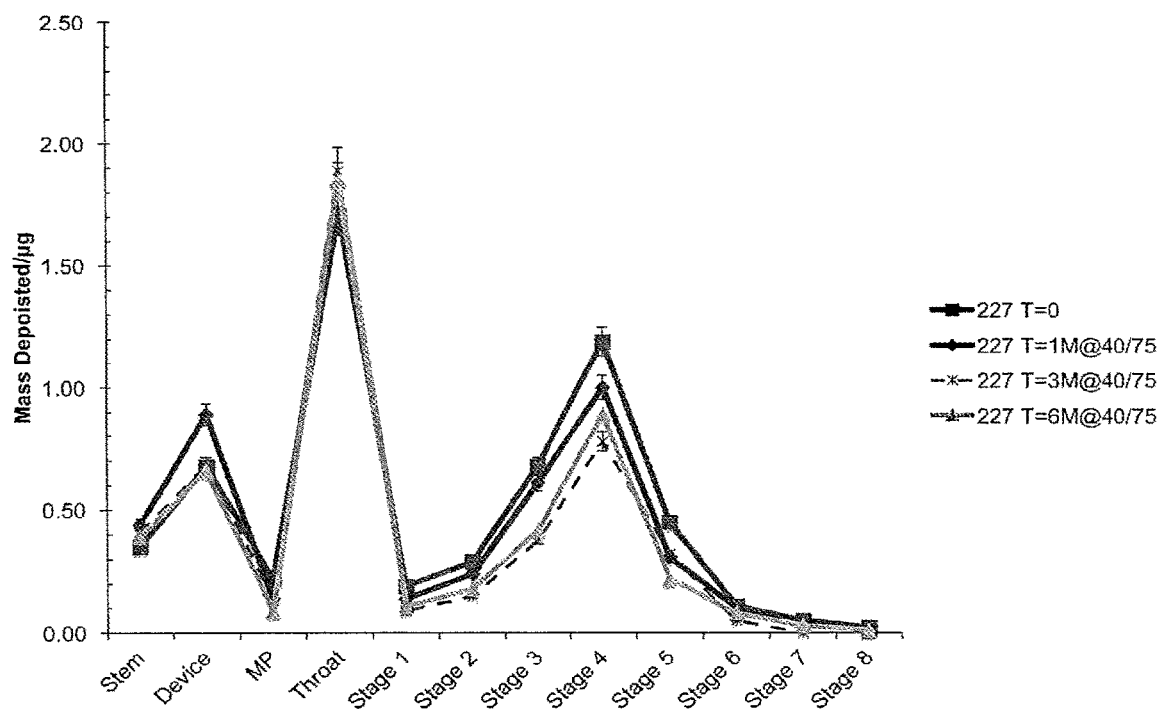
B
Figure 4. APSD profile of budesonide (A) and formoterol (B) actuated from a combination budesonide/formoterol formulation in HFA 227ea actuated into a NGI at 30 L.min$^{-1}$.

PHARMACEUTICAL COMPOSITION

CROSS REFERENCE TO RELATED APPLICATIONS

This application is a continuation of U.S. patent application Ser. No. 15/781,045, filed Jun. 1, 2018, which is a 371 national phase of PCT/GB16/053812, filed Dec. 2, 2016, which claims the benefit of the filing date of GB Application No. 1521456.2, filed Dec. 4, 2015 and GB Application No. 1615916.2, filed Sep. 19, 2016, the disclosures of which are incorporated, in their entirety, by this reference.

FIELD

The present invention relates to the delivery of drug formulations from a medical device, such as a metered dose inhaler (MDI), using a propellant comprising 1,1-difluoroethane (HFA-152a). More particularly, the present invention relates to pharmaceutical compositions comprising R-152a propellant and a binary drug formulation which is dissolved or suspended in the propellant and to medical devices containing those compositions. The pharmaceutical compositions of the invention are particularly suited for delivery from a pressurised aerosol container using a metered dose inhaler (MDI).

BACKGROUND

MDIs are the most significant type of inhalation drug delivery system and are well known to those skilled in the art. They are designed to deliver, on demand, a discrete and accurate amount of a drug to the respiratory tract of a patient using a liquefied propellant in which the drug is dissolved, suspended or dispersed. The design and operation of MDIs is described in many standard textbooks and in the patent literature. They all comprise a pressurised container that holds the drug formulation, a nozzle and a valve assembly that is capable of dispensing a controlled quantity of the drug through the nozzle when it is activated. The nozzle and valve assembly are typically located in a housing that is equipped with a mouth piece. The drug formulation will comprise a propellant, in which the drug is dissolved, suspended or dispersed, and may contain other materials such as polar excipients, surfactants and preservatives.

In order for a propellant to function satisfactorily in MDIs, it needs to have a number of properties. These include an appropriate boiling point and vapour pressure so that it can be liquefied in a closed container at room temperature but develop a high enough pressure when the MDI is activated to deliver the drug as an atomised formulation even at low ambient temperatures. Further, the propellant should be of low acute and chronic toxicity and have a high cardiac sensitisation threshold. It should have a high degree of chemical stability in contact with the drug, the container and the metallic and non-metallic components of the MDI device, and have a low propensity to extract low molecular weight substances from any elastomeric materials in the MDI device. The propellant should also be capable of maintaining the drug in a homogeneous solution, in a stable suspension or in a stable dispersion for a sufficient time to permit reproducible delivery of the drug in use. When the drug is in suspension in the propellant, the density of the liquid propellant is desirably similar to that of the solid drug in order to avoid rapid sinking or floating of the drug particles in the liquid. Finally, the propellant should not present a significant flammability risk to the patient in use. In particular, it should form a non-flammable or low flammability mixture when mixed with air in the respiratory tract.

Dichlorodifluoromethane (R-12) possesses a suitable combination of properties and was for many years the most widely used MDI propellant, often blended with trichlorofluoromethane (R-11). Due to international concern that fully and partially halogenated chlorofluorocarbons (CFCs), such as dichlorodifluoromethane and trichlorofluoromethane, were damaging the earth's protective ozone layer, many countries entered into an agreement, the Montreal Protocol, stipulating that their manufacture and use should be severely restricted and eventually phased out completely. Dichlorodifluoromethane and trichlorofluoromethane were phased out for refrigeration use in the 1990's, but are still used in small quantities in the MDI sector as a result of an essential use exemption in the Montreal Protocol.

1,1,1,2-tetrafluoroethane (R-134a) was introduced as a replacement refrigerant and MDI propellant for R-12. 1,1,1,2,3,3,3-heptafluoropropane (R-227ea) was also introduced as a replacement propellant for dichlorotetrafluoroethane (R-114) in the MDI sector and is sometimes used alone or blended with R-134a for this application.

Although R-134a and R-227ea have low ozone depletion potentials (ODPs), they have global warming potentials (GWPs), 1430 and 3220 respectively, which are now considered to be too high by some regulatory bodies, especially for dispersive uses when they are released into the atmosphere.

One industrial area that has received particular attention recently has been the automotive air-conditioning sector where the use of R-134a has come under regulatory control as a result of the European Mobile Air Conditioning Directive (2006/40/EC). Industry is developing a number of possible alternatives to R-134a in automotive air conditioning and other applications that have a low greenhouse warming potential (GWP) as well as a low ozone depletion potential (ODP). Many of these alternatives include hydrofluoropropenes, especially the tetrafluoropropenes, such as 2,3,3,3-tetrafluoropropene (R-1234yf) and 1,3,3,3-tetrafluoropropene (R-1234ze).

Although the proposed alternatives to R-134a have a low GWP, the toxicological status of many of the components, such as certain of the fluoropropenes, is unclear and they are unlikely to be acceptable for use in the MDI sector for many years, if at all.

There are also other problems with R-134a and R-227ea. Most pharmaceutical actives for treating respiratory disorders, such as asthma, tend not to dissolve well in either R-134a or R-227ea and have to be handled as suspensions in the propellant. Drug suspensions give rise to a number of problems, such as nozzle blockage, agglomeration and sedimentation, the latter problem making it essential to shake the MDI thoroughly before use to ensure that the drug is evenly distributed in the propellant. Furthermore, if the pharmaceutical active settles quickly following re-suspension in the propellant, as is often the case, then the propellant/drug composition must be delivered from the MDI shortly after shaking in order to ensure that the dose that is delivered contains an effective concentration of the pharmaceutical active.

The problem of poorly dissolving drugs has been addressed by including a polar excipient in the composition which either helps to dissolve the drug to form a solution or else enhances wetting of suspended drug particles to yield a better dispersed and more stable suspension. A preferred polar excipient is ethanol. However, the use of large amounts of ethanol can tend to result in a coarse spray having droplet sizes that are too large for acceptable penetration into the deep bronchiole passages of the lung. Further, high levels of ethanol can have unacceptable irritancy to the mouth and throat, especially with younger users and may be unacceptable on religious grounds.

Surfactants have also been included in some formulations that include drugs that are either insoluble or only sparingly soluble in the propellant, as these can also help to produce a more stable suspension. However, surfactants must be selected carefully for acceptability in the lung and add an additional layer of formulation complexity. Accordingly, it would be beneficial to form a stable suspension without the use of a surfactant.

A commonly used drug for treating asthma and chronic obstructive pulmonary disease (COPD) is formoterol, most commonly in the form of its dihydrate fumarate salt. Formoterol is a selective, long-acting $\beta_2$-adrenergic agonist (LABA) that can be delivered to the respiratory tract using a MDI. Unfortunately, it has proven difficult to formulate formoterol in a form that is suitable for delivery using MDI technology due to its limited physical and chemical stability. The problem of stability is particularly evident when the formoterol is exposed to other components that are often used in pharmaceutical formulations, including excipients, solvents, e.g. ethanol, and other therapeutic agents. Other therapeutic agents that are used in combination with formoterol include corticosteroids and more particularly the glucocorticosteroids. Particularly desirable combination formulations include formoterol with one or more corticosteroids selected from mometasone (often as the furoate), budesonide, beclomethasone (often as the dipropionate) and fluticasone (often as the propionate).

The instability of pharmaceutical formulations of formoterol can result in a limited shelf life at ambient temperatures and can necessitate refrigerated storage prior to use.

BRIEF DESCRIPTION OF THE FIGURES

FIG. 1 shows the APSD profile of budesonide (A) and formoterol (B) actuated from a combination budesonide/formoterol formulation in HFA 152a actuated into a NGI at 30 $Lmin^{-1}$;

FIG. 2 shows the APSD profile of budesonide (A) and formoterol (8) actuated from a combination budesonide/formoterol formulation in HFA 227ea actuated into a NGI at 30 $Lmin^{-1}$;

FIG. 3 shows the APSD profile of budesonide (A) and formoterol (B) actuated from a combination budesonide/formoterol formulation in HFA 152a actuated into a NGI at 30 30 $Lmin^{-1}$; and FIG. 4 shows the APSD profile of budesonide (A) and formoterol (B) actuated from a combination budesonide/formoterol formulation in HFA 227ea actuated into a NGI at 30 $Lmin^{-1}$.

DETAILED DESCRIPTION

There is a need for a pharmaceutical composition of formoterol and a corticosteroid, especially budesonide, which can be delivered using a MDI and that uses a propellant having a reduced GWP in comparison with R-134a and R-227ea. There is also a need for a pharmaceutical composition of formoterol and a corticosteroid, especially budesonide, which exhibits improved storage stability.

According to a first aspect of the present invention, there is provided a pharmaceutical composition, e.g. a pharmaceutical suspension or a pharmaceutical solution, said composition comprising:

(i) at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol;
(ii) at least one corticosteroid, especially budesonide;
(iii) a surfactant component comprising at least one surfactant compound, especially at least one surfactant compound selected from polyvinylpyrrolidone and polyethylene glycols; and
(iv) a propellant component comprising 1,1-difluoroethane (R-152a).

The pharmaceutical composition of the first aspect of the invention typically contains less than 500 ppm of water based on the total weight of the pharmaceutical composition. In a preferred embodiment, the pharmaceutical composition of the first aspect of the invention contains less than 100 ppm, preferably less than 50 ppm, more preferably less than 10 ppm and particularly less than 5 ppm of water based on the total weight of the pharmaceutical composition. In referring to the water content of the pharmaceutical composition, we are referring to the content of free water in the composition and not any water that happens to be present in any hydrated drug compounds that may be used as part of the drug component. In an especially preferred embodiment, the pharmaceutical composition is water-free. Alternatively, the pharmaceutical composition of the first aspect may contain greater than 0.5 ppm of water, e.g. 1 ppm or greater, but less than the amounts discussed above, as it can in practice be difficult to remove all the water from the composition and then retain it in such a water-free state. Low water contents are preferred because they tend to reduce the degradation of the drug compounds resulting in a composition with higher chemical stability.

Accordingly a preferred embodiment of the first aspect of the present invention provides a pharmaceutical composition, e.g. a pharmaceutical suspension or a pharmaceutical solution, said composition comprising:

(i) at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol;
(ii) at least one corticosteroid, especially budesonide;
(iii) a surfactant component comprising at least one surfactant compound, especially at least one surfactant compound selected from polyvinylpyrrolidone and polyethylene glycols; and
(iv) a propellant component comprising 1,1-difluoroethane (R-152a), wherein the composition contains less than 100 ppm, preferably less than 50 ppm, more preferably less than 10 ppm and particularly less than 5 ppm of water based on the total weight of the pharmaceutical composition.

In a preferred embodiment, the pharmaceutical composition of the first aspect of the invention contains less than 1000 ppm, preferably less than 500 ppm, more preferably less than 100 ppm and particularly less than 50 ppm of dissolved oxygen based on the total weight of the pharmaceutical composition. In an especially preferred embodiment, the pharmaceutical composition is oxygen-free. Alternatively, the pharmaceutical composition of the first aspect may contain greater than 0.5 ppm of oxygen, e.g. 1 ppm or greater, but less than the amounts discussed above, as it can in practice be difficult to retain the composition in an oxygen-free state. Low oxygen contents are preferred because they tend to reduce the degradation of the drug compounds resulting in a composition with higher chemical stability.

Accordingly a preferred embodiment of the first aspect of the present invention provides a pharmaceutical composition, e.g. a pharmaceutical suspension or a pharmaceutical solution, said composition comprising:
(i) at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol;
(ii) at least one corticosteroid, especially budesonide;
(iii) a surfactant component comprising at least one surfactant compound, especially at least one surfactant compound selected from polyvinylpyrrolidone and polyethylene glycols; and
(iv) a propellant component comprising 1,1-difluoroethane (R-152a),
wherein the composition contains less than 1000 ppm, preferably less than 500 ppm, more preferably less than 100 ppm and particularly less than 50 ppm of oxygen based on the total weight of the pharmaceutical composition.

The pharmaceutical composition of the present invention is suitable for delivery to the respiratory tract using a metered dose inhaler (MDI).

In one embodiment, the pharmaceutical composition of the first aspect of the present invention additionally includes a polar excipient, such as ethanol. Polar excipients are used routinely in pharmaceutical compositions for treating respiratory disorders that are delivered using metered dose inhalers (MDIs). They are also referred to as solvents, co-solvents, carrier solvents and adjuvants. Their inclusion can serve to solubilise the surfactant or the drug in the propellant and/or inhibit deposition of drug particles on the surfaces of the metered dose inhaler that are contacted by the pharmaceutical composition as it passes from the container in which it is stored to the nozzle outlet. They are also used as bulking agents in two-stage filling processes where the drug is mixed with a suitable polar excipient. The most commonly used polar excipient is ethanol. If a polar excipient is used, it will typically be present in an amount of from 0.5 to 10% by weight, preferably in an amount of from 1 to 5% by weight based on the total weight of the pharmaceutical composition.

In a preferred embodiment, the pharmaceutical composition of the first aspect of the present invention is free of polar excipients such as ethanol.

The pharmaceutical composition of the first aspect of the present invention preferably consists essentially of and more preferably consists entirely of the four components (i) to (iv) listed above. By the term "consists essentially of", we mean that at least 95 weight %, more preferably at least 98 weight % and especially at least 99 weight % of the pharmaceutical composition consists of the four listed components.

The at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol, hereinafter the at least one formoterol compound, and the at least one corticosteroid may be dispersed or suspended in the propellant. The drug particles in such suspensions preferably have a diameter of less than 100 microns, e.g. less than 50 microns. However, in an alternative embodiment the pharmaceutical compositions of the invention are solutions with the at least one formoterol compound and the at least one corticosteroid dissolved in the propellant, optionally, although not usually, with the assistance of a polar excipient, such as ethanol.

The at least one formoterol compound and the at least one corticosteroid in the pharmaceutical composition of the invention in all aspects and embodiments disclosed herein are preferably in a micronized form. Further, the pharmaceutical composition of the invention in all aspects and embodiments disclosed herein is preferably free of perforated microstructures.

Suitable pharmaceutically acceptable salts of formoterol include acid addition salts derived from organic and inorganic acids, such as the hydrochloride, sulphate, phosphate, maleate, fumarate, tartrate, citrate, benzoate, methoxybenzoate, hydroxybenzoate, chlorobenzoate, p-toluenesulphonate, methanesulphonate, ascorbate, salicylate, acetate, succinate, lactate, glutarate, gluconate and oleate. The fumarate salt of formoterol is preferred and in a particularly preferred embodiment the pharmaceutical composition of the invention includes formoterol fumarate dihydrate. Especially preferred pharmaceutical compositions are those in which the at least one formoterol compound consists essentially of formoterol fumarate dihydrate. By the term "consists essentially of", we mean that at least 95 weight %, more preferably at least 98 weight % and especially at least 99 weight % of the at least one formoterol compound is formoterol fumarate dihydrate. Most preferred are pharmaceutical compositions in which the at least one formoterol compound is entirely formoterol fumarate dihydrate.

The pharmaceutical compositions of the invention also include a corticosteroid. Any of the corticosteroids that have been in use hitherto for treating asthma and chronic obstructive pulmonary diseases and that can be delivered using a MDI can be used in the pharmaceutical compositions of the present invention. Suitable corticosteroids include budesonide, mometasone, beclomethasone and fluticasone as well as their pharmaceutically acceptable salts. Preferred compounds include budesonide, mometasone furoate, beclomethasone dipropionate and fluticasone propionate. The most preferred corticosteroids are budesonide, mometasone, fluticasone and beclomethasone, particularly budesonide and mometasone and especially budesonide.

Especially preferred pharmaceutical compositions are those in which the at least one corticosteroid consists essentially of budesonide. By the term "consists essentially of", we mean that at least 95 weight %, more preferably at least 98 weight % and especially at least 99 weight % of the at least one corticosteroid is budesonide. Most preferred are pharmaceutical compositions in which the at least one corticosteroid is entirely budesonide.

Accordingly, in a preferred embodiment, the pharmaceutical composition of the invention comprises both formoterol fumarate dihydrate and budesonide. Preferably, formoterol fumarate dihydrate and budesonide are the only pharmaceutical actives in the pharmaceutical composition of the invention.

The weight ratio of the at least one formoterol compound, e.g. formoterol fumarate dihydrate, to the budesonide is typically in the range of from 1:4 to 1:70.

The propellant component in the pharmaceutical composition of the present invention comprises 1,1-difluoroethane (R-152a). Thus, we do not exclude the possibility that the propellant component may include other propellant compounds in addition to the R-152a. For example, the propellant component may additionally comprise one or more additional hydrofluorocarbon or hydrocarbon propellant compounds, e.g. selected from R-227ea, R-134a, difluoromethane (R-32), propane, butane, isobutane and dimethyl ether. The preferred additional propellants are R-227ea and R-134a.

If an additional propellant compound is included, such as R-134a or R-227ea, at least 5% by weight and preferably at least 10% by weight of the propellant component should be R-152a. Typically, the R-152a will constitute at least 90 weight %, e.g. from 90 to 99 weight %, of the propellant component. Preferably, the R-152a will constitute at least 95 weight %, e.g. from 95 to 99 weight %, and more preferably at least 99 weight % of the propellant component.

In an especially preferred embodiment, the propellant component consists entirely of HFA-152a so that the pharmaceutical composition of the invention comprises HFA-152a as the sole propellant. By the term "consists entirely of" we do not, of course, exclude the presence of minor amounts, e.g. up to a few hundred parts per million, of impurities that may be present following the process that is used to make the HFA-152a providing that they do not affect the suitability of the propellant in medical applications. Preferably the HFA-152a propellant will contain no more than 10 ppm, e.g. from 0.5 to 10 ppm, more preferably no more than 5 ppm, e.g. from 1 to 5 ppm, of unsaturated impurities, such as vinyl fluoride, vinyl chloride, vinylidene fluoride and chloro-fluoro ethylene compounds.

The pharmaceutical composition of the invention also includes a surfactant component comprising at least one surfactant compound. Surfactant compounds of the type that have been in use hitherto in pharmaceutical formulations for MDIs may be used in the pharmaceutical compositions of the present invention. Preferred surfactants are selected from polyvinylpyrrolidone, polyethylene glycol surfactants, oleic acid and lecithin. In a preferred embodiment, the surfactant component consists essentially of and still more preferably consists entirely of at least one surfactant compound selected from polyvinylpyrrolidone, polyethylene glycols, oleic acid and lecithin. In a particularly preferred embodiment, the surfactant component consists essentially of and still more preferably consists entirely of at least one surfactant compound selected from polyvinylpyrrolidone and polyethylene glycols. By the term "consists essentially of", we mean that at least 95 weight %, more preferably at least 98 weight % and especially at least 99 weight % of the surfactant component is composed of the listed surfactants. In an especially preferred embodiment, the surfactant component includes both polyvinylpyrrolidone and a polyethylene glycol surfactant.

It will be apparent from the discussion above that in a preferred embodiment of the present invention, there is provided a pharmaceutical composition comprising:
(i) formoterol fumarate dihydrate;
(ii) budesonide;
(iii) a surfactant component comprising at least one surfactant compound selected from polyvinylpyrrolidone and polyethylene glycols; and
(iv) a propellant component comprising 1,1-difluoroethane (R-152a).

In this preferred embodiment, the pharmaceutical composition preferably consists essentially of and more preferably is composed entirely of the four listed components (i) to (iv). In addition, the surfactant component preferably consists essentially of and more preferably consists entirely of at least one surfactant compound selected from polyvinylpyrrolidone and polyethylene glycols. Mixtures of polyvinylpyrrolidone and a polyethylene glycol surfactant are preferred. Finally, the propellant component preferably consists essentially of and more preferably consists entirely of 1,1-difluoroethane (R-152a).

The pharmaceutical composition of the present invention typically comprises from 0.01 to 1.0 weight % of the at least one formoterol compound and the at least one corticosteroid combined, from 96.5 to 99.98 weight % of the propellant component and from 0.01 to 2.5 weight % of the surfactant component. Preferred compositions comprise from 0.05 to 0.5 weight % of the at least one formoterol compound and the at least one corticosteroid combined, from 97.5 to 99.85 weight % of the propellant component and from 0.1 to 2.0 weight % of the surfactant component. Particularly preferred pharmaceutical compositions comprise from 0.07 to 0.2 weight % of the at least one formoterol compound and the at least one corticosteroid combined, from 98.8 to 99.73 weight % of the propellant component and from 0.2 to 1.0 weight % of the surfactant component. All percentages are based on the total weight of the pharmaceutical compositions.

It has been found that the use of propellants comprising 1,1-difluoroethane (R-152a) in pharmaceutical compositions containing a formoterol compound, such as formoterol fumarate dihydrate, can unexpectedly improve the chemical stability of the formoterol compound compared to the stability it exhibits in known formulations containing either R-134a or R-227ea as the propellant.

Accordingly, in a second aspect of the present invention there is provided a method of stabilising a pharmaceutical composition comprising a propellant and at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol which is dissolved or suspended in the propellant, said method comprising using as the propellant a propellant component comprising 1,1-difluoroethane (R-152a).

The improved chemical stability can result, in particular, when the pharmaceutical composition contains less than 500 ppm, preferably less than 100 ppm, more preferably less than 50 ppm, still more preferably less than 10 ppm and particularly less than 5 ppm of water based on the total weight of the pharmaceutical composition. In referring to the water content of the pharmaceutical composition, we are referring to the content of free water in the composition and not any water that happens to be present in any hydrated drug compounds that may be used as part of the drug component. In an especially preferred embodiment, the pharmaceutical composition is water-free. Alternatively, the pharmaceutical composition recited in the second aspect of the present invention may contain greater than 0.5 ppm of water, e.g. greater than 1 ppm, but less than the amounts discussed above, as it can in practice be difficult to remove all the water from the composition and then retain it in such a water-free state.

Accordingly, in a preferred embodiment of the second aspect of the present invention there is provided a method of improving the stability of a pharmaceutical composition comprising a propellant and at least one formoterol compound selected from formoterol, pharmaceutically acceptable salts of formoterol, prodrugs of formoterol, solvates of formoterol, solvates of pharmaceutically acceptable salts of formoterol and solvates of prodrugs of formoterol which is dissolved or suspended in the propellant, said method comprising using as the propellant a propellant component comprising 1,1-difluoroethane (R-152a) and selecting the components and conditions for the preparation of the pharmaceutical composition to maintain the water content of the pharmaceutical composition below 100 ppm, preferably below 50 ppm, more preferably below 10 ppm and particularly below 5 ppm based on the total weight of the pharmaceutical composition.

In practice, preparing a pharmaceutical composition with the low water levels recited above involves using a propellant component with a suitably low water content, as it is usually the largest mass item in the finished device, and then preparing the pharmaceutical composition under suitably dry conditions, e.g. in a dry nitrogen atmosphere. Preparing pharmaceutical compositions under dry conditions is well known and the techniques involved are well understood by those skilled in the art. Other steps to obtain a low water content in the finished device include drying and storing the can and valve components in a moisture-controlled atmosphere, e.g. dry nitrogen or air, prior to and during device assembly. If the pharmaceutical composition contains a significant amount of ethanol, then it may also be important to control the water content of the ethanol as well as the propellant, e.g. by drying to reduce the water content to suitably low levels. Suitable drying techniques are well known to those skilled in the art and include the use of a molecular sieve or other inorganic desiccant and membrane drying processes.

In the stabilisation method of the second aspect of the present invention suitable and preferred formoterol compounds are as described for the pharmaceutical composition of the first aspect of the present invention. In addition, suitable and preferred propellant components are as described for the pharmaceutical composition of the first aspect of the present invention.

In preferred stabilisation methods of the second aspect of the present invention, the pharmaceutical composition additionally comprises at least one corticosteroid and/or a surfactant component comprising at least one surfactant compound. When a corticosteroid and/or surfactant component are included, suitable and preferred corticosteroids and suitable and preferred surfactant compounds are as described for the pharmaceutical composition of the first aspect of the present invention.

In one preferred stabilisation method, the resulting pharmaceutical composition after storage at 40° C. and 75% relative humidity for 1 month will produce less than 0.3% by weight, preferably less than 0.2% by weight and more preferably less than 0.1% by weight of impurities from the degradation of the at least one formoterol compound based on the total weight of the at least one formoterol compound and the impurities.

In another preferred stabilisation method in which the pharmaceutical composition also comprises at least one corticosteroid, the resulting pharmaceutical composition after storage at 40° C. and 75% relative humidity for 1 month will produce less than 0.3% by weight, preferably less than 0.2% by weight and more preferably less than 0.1% by weight of impurities from the degradation of the at least one formoterol compound and the at least one corticosteroid based on the total weight of the at least one formoterol compound, the at least one corticosteroid and the impurities.

In a further preferred stabilisation method, the resulting pharmaceutical composition after storage at 40° C. and 75% relative humidity for 3 months will produce less than 0.7% by weight, preferably less than 0.5% by weight and more preferably less than 0.3% by weight of impurities from the degradation of the at least one formoterol compound based on the total weight of the at least one formoterol compound and the impurities.

In yet another preferred stabilisation method in which the pharmaceutical composition also comprises at least one corticosteroid, the resulting pharmaceutical composition after storage at 40° C. and 75% relative humidity for 3 months will produce less than 0.7% by weight, preferably less than 0.5% by weight and more preferably less than 0.3% by weight of impurities from the degradation of the at least one formoterol compound and the at least one corticosteroid based on the total weight of the at least one formoterol compound, the at least one corticosteroid and the impurities.

In yet another preferred stabilisation method, at least 99.0% by weight, preferably at least 99.5% by weight and more preferably at least 99.7% by weight of the at least one formoterol compound that is contained originally in the pharmaceutical composition immediately following preparation will be present in the composition after storage at 40° C. and 75% relative humidity for 3 months.

In still another preferred stabilisation method in which the pharmaceutical composition also comprises at least one corticosteroid, at least 99.0% by weight, preferably at least 99.5% by weight and more preferably at least 99.7% by weight of the at least one formoterol compound and the at least one corticosteroid that are contained originally in the pharmaceutical composition immediately following preparation will be present in the composition after storage at 40° C. and 75% relative humidity for 3 months.

In a further preferred stabilisation method, at least 99.0%, preferably at least 99.5% and more preferably at least 99.7% of the original pharmaceutical activity of the composition is retained after storage at 40° C. and 75% relative humidity for 3 months.

One preferred pharmaceutical composition of the first aspect of the present invention will produce less than 0.3% by weight, preferably less than 0.2% by weight and more preferably less than 0.1% by weight, e.g. less than 0.05% by weight, of total impurities from the degradation of the pharmaceutical actives, i.e. the at least one formoterol compound and the at least one corticosteroid, after storage at 40° C. and 75% relative humidity for 1 month.

Another preferred pharmaceutical composition of the first aspect of the present invention will produce less than 0.7% by weight, preferably less than 0.5% by weight and more preferably less than 0.3% by weight of total impurities from the degradation of the pharmaceutical actives, i.e. the at least one formoterol compound and the at least one corticosteroid, after storage at 40° C. and 75% relative humidity for 3 months.

The weight % of impurities indicated above are based on the total weight of the at least one formoterol compound, the at least one corticosteroid and the impurities. In a further preferred pharmaceutical composition of the first aspect of the present invention at least 99.0% by weight, preferably at least 99.5% by weight and more preferably at least 99.7% by weight of the at least one formoterol compound and the at least one corticosteroid that are contained originally in the pharmaceutical composition of the invention immediately following preparation will be present in the composition after storage at 40° C. and 75% relative humidity for 3 months.

In yet another preferred pharmaceutical composition of the first aspect of the present invention at least 99.0%, preferably at least 99.5% and more preferably at least 99.7% of the original pharmaceutical activity of the pharmaceutical composition of the invention is retained after storage at 40° C. and 75% relative humidity for 3 months.

In referring to the storage of the pharmaceutical compositions in the above described stabilisation methods, we are referring, in particular, to the storage of those compositions in uncoated aluminium containers. Similarly, in referring to the storage of the above described pharmaceutical compositions, we are referring, in particular, to their storage in uncoated aluminium containers.

The pharmaceutical composition of the invention finds particular utility in the delivery of the formoterol and corticosteroid compounds from a pressurised aerosol container, e.g. using a metered dose inhaler (MDI). For this application, the pharmaceutical composition is contained in the pressurised aerosol container and the R-152a propellant functions to deliver the drug as a fine aerosol spray.

The pharmaceutical composition of the invention may comprise one or more other additives of the type that are conventionally used in drug formulations for pressurised MDIs, such as valve lubricants. Where other additives are included in the pharmaceutical composition, they are normally used in amounts that are conventional in the art.

The pharmaceutical composition of the invention is normally stored in a pressurised container or canister which is to be used in association with a medication delivery device. When so stored, the pharmaceutical composition is normally a liquid. In a preferred embodiment, the pressurised container is designed for use in a metered dose inhaler (MDI). In a particularly preferred embodiment, the pressurised container is a coated aluminium can or an uncoated aluminium can, especially the latter.

Accordingly, a third aspect of the present invention provides a pressurised container holding the pharmaceutical composition of the first aspect of the present invention. In a fourth aspect, the present invention provides a medication delivery device, especially a metered dose inhaler, having a pressurised container holding the pharmaceutical composition of the first aspect of the present invention.

The metered dose inhaler typically comprises a nozzle and valve assembly that is crimped to a container holding the pharmaceutical composition to be dispensed. An elastomeric gasket is used to provide a seal between the container and the nozzle/valve assembly. Preferred elastomeric gasket materials are EPDM, chlorobutyl, bromobutyl and cycloolefin copolymer rubbers as these can exhibit good compatibility with HFA-152a and also provide a good barrier to prevent or limit HFA-152a permeating from the container.

The pharmaceutical composition of the present invention is for use in medicine for treating a patient suffering or likely to suffer from a respiratory disorder and especially asthma or a chronic obstructive pulmonary disease.

Accordingly, the present invention also provides a method for treating a patient suffering or likely to suffer from a respiratory disorder, especially asthma or a chronic obstructive pulmonary disease, which comprises administering to the patient a therapeutically or prophylactically effective amount of a pharmaceutical composition as discussed above. The pharmaceutical composition is preferably delivered to the patient using a MDI.

The pharmaceutical composition of the invention can be prepared and the MDI devices filled using techniques that are standard in the art, such as pressure filling and cold filling. For example, the pharmaceutical composition can be prepared by a simple blending operation in which the at least one formoterol compound, the at least one corticosteroid, the surfactant component and the R-152a-containing propellant are mixed together in the required proportions in a suitable mixing vessel. Mixing can be promoted by stirring as is common in the art. Conveniently, the R-152a-containing propellant is liquefied to aid mixing. If the pharmaceutical composition is made in a separate mixing vessel, it can then be transferred to pressurised containers for storage, such as pressurised containers that are used as part of medication delivery devices and especially MDIs.

The pharmaceutical compositions of the invention can also be prepared within the confines of a pressurised container, such as an aerosol canister or vial, from which the compositions are ultimately released as an aerosol spray using a medication delivery device, such as a MDI. In this method, a weighed amount of the at least one formoterol compound and the at least one corticosteroid is introduced into the open container. A valve is then crimped onto the container and the 152a-containing propellant component, in liquid form, introduced through the valve into the container under pressure, optionally after first evacuating the container through the valve. The surfactant component can be mixed with the formoterol and corticosteroid drugs or, alternatively, introduced into the container after the valve has been fitted, either alone or as a premix with the propellant component. The whole mixture can then be treated to disperse the drugs in the propellant/surfactant mixture, e.g. by vigorous shaking or using an ultrasonic bath. Suitable containers may be made of plastics, metal, e.g. aluminium, or glass. Preferred containers are made of metal, especially aluminium which may be coated or uncoated. Uncoated aluminium containers are especially preferred.

The container may be filled with enough of the pharmaceutical composition to provide for a plurality of dosages. The pressurized aerosol canisters that are used in MDIs typically contain 50 to 150 individual dosages.

The present invention is now illustrated but not limited by the following examples.

Example 1

A number of experiments were conducted to investigate the in vitro aerosolization performance of combination drug formulations of budesonide and formoterol fumarate dihydrate in metered dose inhalers (MDIs) containing either HFA-227ea or HFA-152a as the propellant.

Combination MDI aerosol formulations of budesonide and formoterol were prepared with polyvinylpyrrolidone K25, PEG 1000 and either HFA-227ea (Solvay Fluor, Germany) or HFA-152a (Mexichem, UK). Each preparation in HFA-227ea or HFA-152a contained micronized budesonide (0.2% w/w), micronized formoterol (0.01% w/w), PEG (0.42% w/w) and PVP (0.001% w/w). The drugs and surfactants were weighed directly into standard uncoated 14 ml aluminium canisters and coated aluminium canisters. The canisters were then crimped with a 63 μL valve (Aptar, France) following which the propellant was filled into the canisters through the valve using a manual Pamasol crimper/filler (Pamasol, Switzerland). Finally, the canisters were sonicated for 20 minutes to aid dispersion of the drug in the suspension.

High performance liquid chromatography (HPLC) was used to determine drug content following aerosolization studies (see below). A 100×3 mm Accucore Phenyl-X column with a 2.6 μm particle size was used for the analysis. The column was coupled to a UV detector operating at a wavelength of 250 nm. The autosampler was operated at ambient temperature and 100 μl samples were injected into the column for the analyses. The chromatographic conditions are shown in Table 1 below.

TABLE 1

| Drug | Pump Flow Rate (ml · min⁻¹) | Mobile Phase (gradient elution) | UV Wavelength (nm) | Column Temperature (° C.) |
|---|---|---|---|---|
| Budesonide and Formoterol Fumarate Dihydrate (Dual detection) | 0.55 | Mobile Phase A: 10 mM Ammonium Formate (adjusted to pH 3.0 with formic acid) Mobile Phase B: Acetonitrile | 250 | 40 |

The composition of the mobile phase was varied as shown in Table 2 below.

TABLE 2

| Time (mins) | Volume % of ammonium formate (pH 3.0) | Volume % of acetonitrile |
|---|---|---|
| 0 | 90 | 10 |
| 16.0 | 0 | 100 |
| 20.0 | 0 | 100 |
| 20.1 | 90 | 10 |
| 25.0 | 90 | 10 |

The in vitro aerosolization performance of the formulations was studied using a Next Generation Impactor (NGI, Copley Scientific, Nottingham UK), which was connected to a vacuum pump (GE Motors, NJ, USA). Prior to testing, the cups of the NGI system were coated with 1% v/v silicone oil in hexane to eliminate particle bounce. For each experiment, three actuations of the valve were discharged into the NGI at 30 L·min⁻¹ as per pharmacopeia guidelines. Following aerosolization, the NGI apparatus was dismantled and the actuator and each part of the NGI was washed down into known volumes of a methanol/water (1:1) diluent. The mass of drug deposited on each part of the NGI was determined by HPLC. This protocol was repeated three times for each canister, following which, the fine particle dose (FPD) and fine particle fraction of the emitted dose ($FPF_{ED}$) were determined.

The in vitro aerosolization performance of budesonide/formoterol combination drug formulations stored in uncoated aluminium cans using either HFA-227ea or HFA-152a as the propellant was determined at time zero (T=0) and after 1 month (T=1M) and 3 months (T=3M) storage (valve down) at 40° C. and 75% relative humidity. The results for budesonide are shown in Table 3 and for formoterol fumarate dihydrate in Table 4. In addition, the aerodynamic particle size distribution (APSD) profile of budesonide and formoterol from HFA-152a and HFA-227ea systems are shown in FIGS. 1A/B and 2A/B, respectively.

TABLE 3

In vitro aerosolization performance of budesonide emitted from MDI combination formulations of budesonide and formoterol in HFA-227ea and HFA-152a in uncoated aluminium cans as characterised by the emitted dose, fine particle dose, fine particle fraction of the emitted dose ($FPF_{ED}$), mass median aerodynamic diameter (MMAD) and geometric standard deviation (GSD).

|  | 227ea T = 0 | 227ea T = 1 M@ 40° C./ 75% RH | 227ea T = 3 M@ 40° C./ 75% RH | 152a T = 0 | 152a T = 1 M@ 40° C./ 75% RH | 152a T = 3 M@ 40° C./ 75% RH |
|---|---|---|---|---|---|---|
| Emitted Dose (µg) | 143.8 (1.5) | 134.7 (2.9) | 135.7 (4.1) | 159.6 (3.2) | 159.8 (6.2) | 155.2 (4.3) |
| Fine particle Dose (µg) | 58.7 (2.8) | 42.2 (3.2) | 38.8 (2.7) | 83.2 (0.9) | 85.4 (0.5) | 75.8 (1.2) |
| % FPF | 40.7 | 31.3 | 28.6 | 52.1 | 53.4 | 48.8 |
| MMAD (µm) | 3.8 | 4.0 | 4.0 | 3.8 | 3.7 | 3.8 |
| GSD | 1.7 | 1.6 | 1.6 | 2.7 | 1.7 | 1.7 |

TABLE 4

In vitro aerosolization performance of formoterol emitted from MDI combination formulations of budesonide and formoterol in HFA-227ea and HFA-152a in uncoated aluminium cans as characterised by the emitted dose, fine particle dose, fine particle fraction of the emitted dose ($FPF_{ED}$), mass median aerodynamic diameter (MMAD) and geometric standard deviation (GSD).

|  | 227ea T = 0 | 227ea T = 1 M@ 40° C./ 75% RH | 227ea T = 3 M@ 40° C./ 75% RH | 152a T = 0 | 152a T = 1 M@ 40° C./ 75% RH | 152a T = 3 M@ 40° C./ 75% RH |
|---|---|---|---|---|---|---|
| Emitted Dose (µg) | 4.5 (0.10) | 4.2 (0.3) | 3.9 (0.2) | 5.2 (0.1) | 5.2 (0.2) | 4.8 (0.2) |
| Fine particle Dose (µg) | 2.1 (0.2) | 1.9 (0.1) | 1.5 (0.1) | 2.7 (0.1) | 2.8 (0.1) | 2.5 (0.1) |
| % FPF | 46.4 | 43.7 | 38.8 | 53.1 | 54.4 | 51.3 |
| MMAD (µm) | 3.6 | 3.7 | 3.7 | 3.2 | 3.2 | 3.4 |
| GSD | 1.9 | 1.8 | 1.9 | 1.9 | 1.9 | 1.9 |

The budesonide component aerosolised using HFA-227ea had an emitted dose of 143.8±1.5 µg, a fine particle dose of 58.7±2.8 µg and a mass median aerodynamic diameter (MMAD) of 3.8 µm. Storage of the formulation under stress stability conditions for 1 month and 3 months resulted in a decline in the fine particle delivery. In contrast, the budesonide component aerosolised using HFA-152a had an emitted dose of 159.6±3.2 µg, a fine particle dose of 83.2±0.9 µg and a MMAD of 3.8 µm. Storage of the HFA-152a based formulation under stress stability conditions for 1 month and 3 months in uncoated aluminium cans did not affect the emitted or fine particle dose from this system.

The formoterol component aerosolised using HFA-227ea had an emitted dose of 4.5±0.1 µg, a fine particle dose of 2.1±0.2 µg and a MMAD of 3.6 µm. Storage of the formulation under stress stability conditions for 1 month and 3 months resulted in a decline in the fine particle delivery. In contrast, the formoterol component aerosolised using HFA-152a had an emitted dose of 5.2±0.1 µg, a fine particle dose of 2.7±0.1 µg and a MMAD of 3.2 µm. Storage of the HFA-152a based formulation under stress stability conditions for 1 month and 3 months in uncoated aluminium cans did not affect the emitted or fine particle dose from this system.

The in vitro aerosolization performance of budesonide/formoterol combination drug formulations stored in coated aluminium cans using either HFA-227ea or HFA-152a as the propellant was determined at time zero (T=0) and after 1 month (T=1M), 3 months (T=3M) and 6 months (T=6M) storage (valve down) at 40° C. and 75% relative humidity. The results for budesonide are shown in Table 5 and for formoterol fumarate dihydrate in Table 6. In addition, the aerodynamic particle size distribution (APSD) profile of budesonide and formoterol from HFA-152a and HFA-227ea systems are shown in FIGS. 3A/B and 4A/B, respectively.

TABLE 5

In vitro aerosolization performance of budesonide emitted from MDI combination formulations of budesonide and formoterol in HFA-227ea and HFA-152a in coated aluminium cans as characterised by the emitted dose, fine particle dose, fine particle fraction of the emitted dose ($FPF_{ED}$), mass median aerodynamic diameter (MMAD) and geometric standard deviation (GSD).

|  | 227ea T = 0 | 227ea T = 1 M@ 40° C./ 75% RH | 227ea T = 3 M@ 40° C./ 75% RH | 227ea T = 6 M@ 40° C./ 75% RH | 152a T = 0 | 152a T = 1 M@ 40° C./ 75% RH | 152a T = 3 M@ 40° C./ 75% RH | 152a T = 6 M@ 40° C./ 75% RH |
|---|---|---|---|---|---|---|---|---|
| Emitted Dose (µg) | 138.3 (1.4) | 135.5 (1.9) | 135.4 (2.6) | 131.8 (0.7) | 153.3 (1.9) | 159.4 (2.3) | 157.3 (3.9) | 155.7 (3.5) |
| Fine particle Dose (µg) | 56.8 (0.2) | 51.1 (0.3) | 37.9 (0.6) | 35.7 (0.4) | 80.0 (0.5) | 84.3 (0.8) | 77.3 (0.6) | 74.3 (0.4) |
| % FPF | 41.1 | 29.6 | 28.0 | 27.1 | 52.0 | 53.0 | 49.1 | 47.7 |
| MMAD (µm) | 3.8 | 4.0 | 4.1 | 4.2 | 3.8 | 3.7 | 3.9 | 3.9 |
| GSD | 1.7 | 1.6 | 1.6 | 1.6 | 1.7 | 1.7 | 1.7 | 1.6 |

TABLE 6

In vitro aerosolization performance of formoterol emitted from MDI combination formulations of budesonide and formoterol in HFA-227ea and HFA-152a in coated aluminium cans as characterised by the emitted dose, fine particle dose, fine particle fraction of the emitted dose ($FPF_{ED}$), mass median aerodynamic diameter (MMAD) and geometric standard deviation (GSD).

|  | 227ea T = 0 | 227ea T = 1 M@ 40° C./ 75% RH | 227ea T = 3 M@ 40° C./ 75% RH | 227ea T = 6 M@ 40° C./ 75% RH | 152a T = 0 | 152a T = 1 M@ 40° C./ 75% RH | 152a T = 3 M@ 40° C./ 75% RH | 152a T = 6 M @ 40° C./ 75% RH |
|---|---|---|---|---|---|---|---|---|
| Emitted Dose (µg) | 4.9 (0.2) | 4.4 (0.2) | 3.8 (0.2) | 3.9 (0.2) | 5.3 (0.1) | 5.3 (0.1) | 5.1 (0.2) | 4.7 (0.2) |
| Fine particle Dose (µg) | 2.3 (0.1) | 1.9 (0.1) | 1.4 (0.2) | 1.4 (0.1) | 2.8 (0.1) | 2.9 (0.1) | 2.7 (0.2) | 2.5 |
| % FPF | 47.3 | 43.3 | 35.9 | 36.0 | 53.2 | 54.1 | 51.8 | 51.3 |
| MMAD (µm) | 3.7 | 3.7 | 3.5 | 3.7 | 3.3 | 3.3 | 3.4 | 3.4 |
| GSD | 2.0 | 1.9 | 1.9 | 1.9 | 1.9 | 2.0 | 2.0 | 1.9 |

The budesonide component aerosolised using HFA-227ea had an emitted dose of 138.3±1.4 µg, a fine particle dose of 56.8±0.2 µg and a mass median aerodynamic diameter (MMAD) of 3.8 µm. Storage of the formulation under stress stability conditions for 1 month, 3 months and 6 months resulted in a significant decline in the fine particle delivery. In contrast, the budesonide component aerosolised using HFA-152a had an emitted dose of 153.3±1.9 µg, a fine particle dose of 80.0±0.5 µg and a MMAD of 3.8 µm. Storage of the HFA-152a based formulation under stress stability conditions for 1 month, 3 months and 6 months in coated aluminium cans did not significantly affect the emitted or fine particle dose from this system.

The formoterol component aerosolised using HFA-227ea had an emitted dose of 4.9±0.2 µg, a fine particle dose of 2.3±0.1 µg and a MMAD of 3.7 µm. Storage of the formulation under stress stability conditions for 1 month, 3 months and 6 months resulted in a significant decline in the fine particle delivery. In contrast, the formoterol component aerosolised using HFA-152a had an emitted dose of 5.3±0.1 µg, a fine particle dose of 2.8±0.1 µg and a MMAD of 3.3 µm. Storage of the HFA-152a based formulation under stress stability conditions for 1 month, 3 months and 6 months in coated aluminium cans did not significantly affect the emitted or fine particle dose from this system.

Example 2

The stability of combination drug formulations of budesonide and formoterol fumarate dihydrate in either HFA-227ea or HFA-152a propellant was investigated at time zero (T=0) and after storage, valve down, for 1 month (T=1M) and 3 months (T=3M) at either 40° C. and 75% relative humidity (RH) or 25° C. and 60% relative humidity (RH) in uncoated aluminium cans.

The stability of the combination drug formulations in HFA-227ea and HFA-152a propellants was also investigated at time zero (T=0) and after storage, valve down, for 1 month (T=1M), 3 months (T=3M) and 6 months (T=6M) at either 40° C. and 75% relative humidity (RH) in coated aluminium cans.

The combination drug formulations were prepared as described in Example 1 above and analysed using the HPLC technique described in Example 1 above.

The results of investigating the chemical stability of the combination drug formulations in HFA-152a and HFA-227ea in uncoated aluminium cans are shown, respectively, in Tables 7 and 8 below.

TABLE 7

Chemical stability of budesonide (BUD) and formoterol fumarate dihydrate (FFD) in HFA-152a in uncoated aluminium cans based on percentage assay and total impurities upon storage at T = 0, T = 1M @ 40° C./75% RH and 25° C./60% RH and T = 3M@ 40° C./75% RH and 25° C./60% RH.

| Time-Point | API | % Assay (LC) | % Total Impurities (BUD + FFD) |
|---|---|---|---|
| T = 0 | BUD[1] | 99.02 | N.D. |
| | FFD[2] | 104.2 | |
| T = 1M@25/60 | BUD | 101.5 | N.D. |
| | FFD | 102.6 | |
| T = 1M@40/75 | BUD | 100.5 | N.D. |
| | FFD | 99.5 | |
| T = 3M@25/60 | BUD | 99.5 | 0.11 |
| | FFD | 100.4 | |
| T = 3M@40/75 | BUD | 99.8 | 0.23 |
| | FFD | 99.9 | |

TABLE 8

Chemical stability of budesonide (BUD) and formoterol fumarate dihydrate (FFD) in HFA-227ea in uncoated aluminium cans based on percentage assay and total impurities upon storage at T = 0, T = 1M @ 40° C./75% RH and 25° C./60% RH and T = 3M@ 40° C./75% RH and 25° C./60 RH %.

| Time-Point | API | % Assay (LC) | % Total Impurities (BUD + FFD) |
|---|---|---|---|
| T = 0 | BUD[1] | 99.02 | N.D. |
| | FFD[2] | 104.2 | |
| T = 1M@25/60 | BUD | 101.5 | 0.33 |
| | FFD | 102.6 | |
| T = 1M@40/75 | BUD | 100.5 | 0.54 |
| | FFD | 99.5 | |
| T = 3M@25/60 | BUD | 98.6 | 0.89 |
| | FFD | 97.6 | |
| T = 3M@40/75 | BUD | 97.2 | 1.26 |
| | FFD | 95.5 | |

The results of investigating the chemical stability of the combination drug formulations in HFA-152a and HFA-227ea in coated aluminium cans are shown, respectively, in Tables 9 and 10 below.

TABLE 9

Chemical stability of budesonide (BUD) and formoterol fumarate dihydrate (FFD) in HFA-152a in coated aluminium cans based on percentage assay and total impurities upon storage at T = 0, T = 1M @ 40° C./75% RH, T = 3M@ 40° C./75% RH and T = 6M@ 40° C./75% RH.

| Time-Point | API | % Assay (LC) | % Total Impurities (BUD + FFD) |
|---|---|---|---|
| T = 0 | BUD[1] | 99.8 | N.D. |
| | FFD[2] | 99.4 | |
| T = 1M@40/75 | BUD | 100.1 | N.D. |
| | FFD | 98.5 | |
| T = 3M@40/75 | BUD | 98.2 | 0.19 |
| | FFD | 98.6 | |
| T = 6M@40/75 | BUD | 98.5 | 0.25 |
| | FFD | 97.9 | |

TABLE 10

Chemical stability of budesonide (BUD) and formoterol fumarate dihydrate (FFD) in HFA-227ea in coated aluminium cans based on percentage assay and total impurities upon storage at T = 0, T = 1M @ 40° C./75% RH, T = 3M@ 40° C./75% RH and T = 6M@ 40° C./75% RH.

| Time-Point | API | % Assay (LC) | % Total Impurities (BUD + FFD) |
|---|---|---|---|
| T = 0 | BUD[1] | 99.02 | N.D. |
| | FFD[2] | 104.2 | |
| T = 1M@40/75 | BUD | 98.5 | 0.29 |
| | FFD | 97.5 | |
| T = 3M@40/75 | BUD | 98.2 | 0.55 |
| | FFD | 97.5 | |
| T = 6M@40/75 | BUD | 97.4 | 1.82 |
| | FFD | 97.2 | |

[1]budesonide
[2]formoterol fumarate dihydrate

For the HFA-152a system in uncoated aluminium cans, no impurities were detected after 1 month and after 3 months the total impurities detected were less than 0.25% by weight. The chemical stability of both drugs in HFA-152a, was therefore, demonstrated over the duration of the stress storage stability tests.

In comparison to the HFA-152a system, for the HFA-227ea system in uncoated cans impurities were detected for both drugs immediately after stress stability storage and after 3 months storage the total impurities exceeded 1% by weight. Hence, the chemical stability profile of both drugs was better in HFA-152a than in HFA-227ea.

For the HFA-152a system in coated aluminium cans, no impurities were detected after 1 month and after 6 months the total impurities detected were only 0.25% by weight. The chemical stability of both drugs in HFA-152a, was therefore, demonstrated over the duration of the stress storage stability tests.

In comparison to the HFA-152a system, for the HFA-227ea system in coated cans impurities were detected for both drugs immediately after stress stability storage and after 6 months storage the total impurities exceeded 1.8% by weight. Hence, the chemical stability profile of both drugs was better in HFA-152a than in HFA-227ea.

Example 3

The suspension stability of budesonide/formoterol combination drug formulations prepared as described in Example 1 was determined using a Turbiscan MA 2000. The Turbiscan instrument has a reading head that moves along a flat-bottomed, 5 mL cylindrical glass cell, and takes readings of transmitted and backscattered light every 40 µm on a maximum sample height of 80 mm. The reading head uses a pulsed near infrared light source and two synchronous detectors. The transmission detector picks up light transmitted through the suspension tube at 0° and back scattering detector receives light back by the product at 135°. In addition, two further formulations were prepared but with the polyvinylpyrrolidone omitted and the suspension stability of those formulations was also examined.

The sedimentation and size of flocs for the different formulations systems are shown in Table 9 below. Formulations with no PVP had larger floc sizes and shorter sedimentation times. These data suggest that PVP improves suspension stability significantly. Of the formulations containing PVP, the HFA-152a formulation had the best suspension stability profile. Thus, the use of a surfactant component comprising polyvinylpyrrolidone and polyethylene glycol surfactants is advantageous.

TABLE 9

Suspension stability profiles of budesonide (BUD) and formoterol (FFD) in combination budesonide/formoterol formulations in HFA 227ea and HFA 152a with and without PVP.

| Formulation | Size Start (microns) | Time to sediment (mins) |
|---|---|---|
| BUD[1]/FFD[2], PEG[3], PVP[4] and HFA-227ea | 3.54 | 1.34 |
| BUD/FFD, PEG, PVP and HFA-152a | 2.85 | 2.00 |
| BUD/FFD, PEG, HFA-227 | 5.25 | <0.5 |
| BUD/FFD, PEG, HFA-152a | 4.29 | <0.5 |

[1]budesonide
[2]formoterol fumarate dihydrate
[3]PEG 1000
[4]polyvinylpyrrolidone

What is claimed is:

1. A pharmaceutical composition comprising:
   (i) at least one compound selected from the group consisting of formoterol, pharmaceutically acceptable salts of formoterol, solvates of formoterol, and solvates of pharmaceutically acceptable salts of formoterol;
   (ii) at least one corticosteroid selected from the group consisting of beclomethasone dipropionate and fluticasone propionate;
   (iii) a surfactant component comprising at least one surfactant compound; and
   (iv) a propellant component comprising at least 90 weight % 1,1-difluoroethane (R-152a);
   wherein the pharmaceutical composition is in the form of a suspension.

2. The pharmaceutical composition of claim 1 further comprising ethanol.

3. The pharmaceutical composition of claim 1 which is free of ethanol.

4. The pharmaceutical composition of claim 1, wherein at least 95 weight % of the pharmaceutical composition consists of the four components (i), (ii), (iii), and (iv).

5. The pharmaceutical composition of claim 1, wherein the pharmaceutical composition consists entirely of the four components (i), (ii), (iii), and (iv).

6. The pharmaceutical composition of claim 1, wherein at least 95 weight % of the propellant component is 1,1-difluoroethane (R-152a).

7. The pharmaceutical composition of claim 6, wherein the propellant component comprises from 0.5 to 10 ppm of unsaturated impurities.

8. The pharmaceutical composition of claim 1, wherein the surfactant component comprises at least one surfactant compound selected from the group consisting of: polyvinylpyrrolidone, polyethylene glycol surfactants, oleic acid, and lecithin.

9. The pharmaceutical composition of claim 1 which after storage in uncoated aluminum containers at 40° C. and 75% relative humidity for 3 months comprises from 0.2% to 0.7% by weight of impurities from the degradation of the at least one compound and the at least one corticosteroid based on the total weight of the at least one compound, the at least one corticosteroid and the impurities.

10. The pharmaceutical composition of claim 9 which after storage in uncoated aluminum containers at 40° C. and 75% relative humidity for 3 months comprises from 0.2% to 0.5% by weight of impurities from the degradation of the at least one compound and the at least one corticosteroid based on the total weight of the at least one compound, the at least one corticosteroid and the impurities.

11. The pharmaceutical composition of claim 1, comprising from 99.7% to 99.0% by weight of the at least one compound and the at least one corticosteroid after storage of the pharmaceutical composition in uncoated aluminum containers at 40° C. and 75% relative humidity for 3 months.

12. The pharmaceutical composition of claim 11, comprising from 99.7% to 99.5% by weight of the at least one compound and the at least one corticosteroid.

13. The pharmaceutical composition of claim 1, further comprising from 0.5 ppm to 500 ppm of water based on the total weight of the pharmaceutical composition.

14. The pharmaceutical composition of claim 1, wherein the pharmaceutical composition comprises from 0.5 ppm to 1000 ppm of oxygen based on the total weight of the pharmaceutical composition.

15. The pharmaceutical composition of claim 1, wherein the at least one compound and the at least one corticosteroid are in a micronized form and wherein the pharmaceutical composition is free of perforated microstructures.

16. A sealed container which is a pressurized aerosol container for use with a metered dose inhaler (MDI) that comprises a pharmaceutical composition as claimed in claim 1.

17. A metered dose inhaler (MDI) fitted with a sealed container as claimed in claim 16.

18. The pharmaceutical composition of claim 1, wherein the at least one compound is formoterol fumarate dihydrate.

19. The pharmaceutical composition of claim 1, further comprising a polar excipient in an amount from 0.5 to 1.0 weight % of the pharmaceutical composition.

20. The pharmaceutical composition of claim 1, wherein the at least one surfactant compound is present in the pharmaceutical composition in an amount from 1.0 to 2.5 weight % of the pharmaceutical composition.

\* \* \* \* \*

UNITED STATES PATENT AND TRADEMARK OFFICE
CERTIFICATE OF CORRECTION

| | | |
|---|---|---|
| PATENT NO. | : 11,559,507 B2 | Page 1 of 1 |
| APPLICATION NO. | : 16/575168 | |
| DATED | : January 24, 2023 | |
| INVENTOR(S) | : Stuart Corr et al. | |

It is certified that error appears in the above-identified patent and that said Letters Patent is hereby corrected as shown below:

In the Specification

Column 19, approx. Line 40, delete "Table 9" and insert in its place --Table 11--.

Column 19, TABLE 9, Line 50, delete "TABLE 9" and insert in its place --TABLE 11--.

Signed and Sealed this
Twenty-ninth Day of August, 2023

Katherine Kelly Vidal
*Director of the United States Patent and Trademark Office*